US005713489A

United States Patent [19]
Loos

[11] Patent Number: 5,713,489
[45] Date of Patent: Feb. 3, 1998

[54] DISPENSER

[75] Inventor: Ralf Loos, München, Germany

[73] Assignee: ROEKO GmbH & Co. Dentalerzeugnisse, Langenau, Germany

[21] Appl. No.: 581,223

[22] Filed: Dec. 29, 1995

[30] Foreign Application Priority Data

Dec. 30, 1994 [DE] Germany ............. 44 47 188.2

[51] Int. Cl.⁶ ............................................. B65G 59/00
[52] U.S. Cl. ........................ 221/205; 221/195; 221/289
[58] Field of Search ............................ 221/188, 189, 221/195, 194, 256, 257, 281, 293, 289, 298, 285; 312/72, 73, 45

[56] References Cited

U.S. PATENT DOCUMENTS

| 918,085 | 4/1909 | Parker | 221/289 |
|---|---|---|---|
| 1,229,982 | 6/1917 | Leonard | 221/205 |
| 1,698,955 | 1/1929 | Lutfring | 221/289 |
| 1,910,209 | 4/1933 | Grunwald | 221/205 |
| 1,916,757 | 7/1933 | Flach | 221/205 |
| 2,342,747 | 2/1944 | Mayer et al. | |
| 2,434,514 | 1/1948 | Penn | 221/205 |
| 2,437,616 | 3/1948 | Satloff | 221/188 |
| 5,046,639 | 9/1991 | Deberry | 221/194 |

FOREIGN PATENT DOCUMENTS

| 715234 | 11/1931 | France | 221/298 |
|---|---|---|---|
| 46483 | 8/1935 | France | |
| 2251197 | 6/1975 | France | |
| 9319912 | 4/1994 | Germany | |
| 281828 | 3/1952 | Switzerland | 221/188 |
| 132430 | 9/1919 | United Kingdom | 221/289 |
| 753593 | 7/1956 | United Kingdom | 221/189 |

Primary Examiner—H. Grant Skaggs
Attorney, Agent, or Firm—Robert W. Becker & Associates

[57] ABSTRACT

An apparatus for dispensing rod-like members that are stored in a parallelepipedal housing. The housing includes a base for carrying the rod-like members, with the base being movable against the force of one or more return springs. The base has a narrow side that extends at least partially through a discharge opening of the housing.

18 Claims, 4 Drawing Sheets

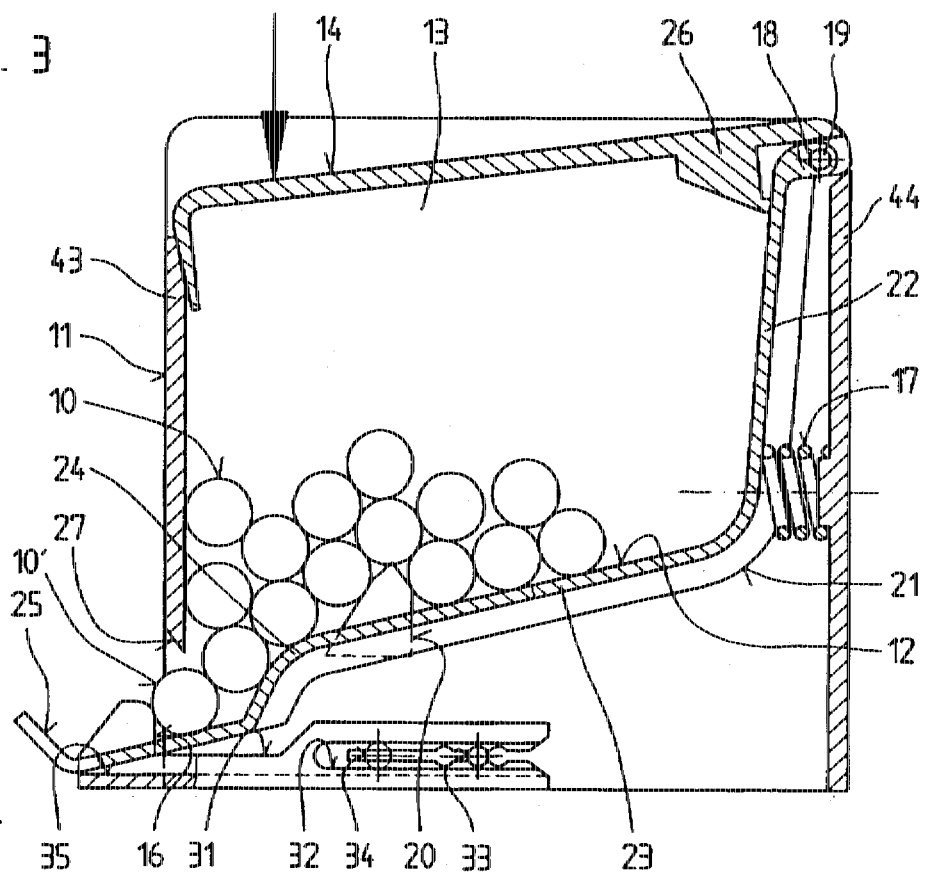

DISPENSER

BACKGROUND OF THE INVENTION

The present invention relates to an apparatus for discharging or dispensing rolls of wadding or similar rod-like members that are stored in a parallelepipedal housing that includes a narrow side that is provided with a discharge opening disposed parallel to the stored rod-like members.

Pursuant to one known dispenser for rolls of wadding, a drawer is provided on the base of the housing; this drawer is provided with a handle so that it can be opened for the manual removal of rolls of wadding. The rolls of wadding are supplied to the drawer via a partition that extends at an angle in the housing. The rolls of wadding can be removed from the open drawer, whereupon the drawer is shoved back into the housing against the action of the rolls of wadding that are stored in the housing.

In addition to the fact that this known apparatus is cumbersome to handle since the drawer must be grasped in order to move it, a drawback of this apparatus is that rolls of wadding that are disposed in the drawer but are not removed therefrom are again returned to the housing. This is not hygienic since when one roll of wadding is removed adjacent rolls are also touched and hence possibly contaminated. If these other rolls of wadding are not removed, they could actually be used during the treatment of a different patient. Furthermore, since the drawer is frequently left open for a longer period of time, dirt and other contamination can enter the dispenser so that the heretofore known apparatus does not ensure a reliable protection against contamination.

It is therefore an object of the present invention to provide an apparatus of the aforementioned general type that is not only extremely easy to operate, but above all ensures that stored rolls of wadding are easy to remove from the housing yet provides a reliable protection against any contamination. Furthermore, manufacturing costs should be kept low and a multi-purpose use with ease of operation should be provided.

BRIEF DESCRIPTION OF THE DRAWINGS

These and other objects and advantages of the present invention will appear more clearly from the following specification in conjunction with the accompanying schematic drawings, in which:

FIGS. 3 and 4 show different operating positions of the apparatus of FIG. 1;

SUMMARY OF THE INVENTION

Figure 1:
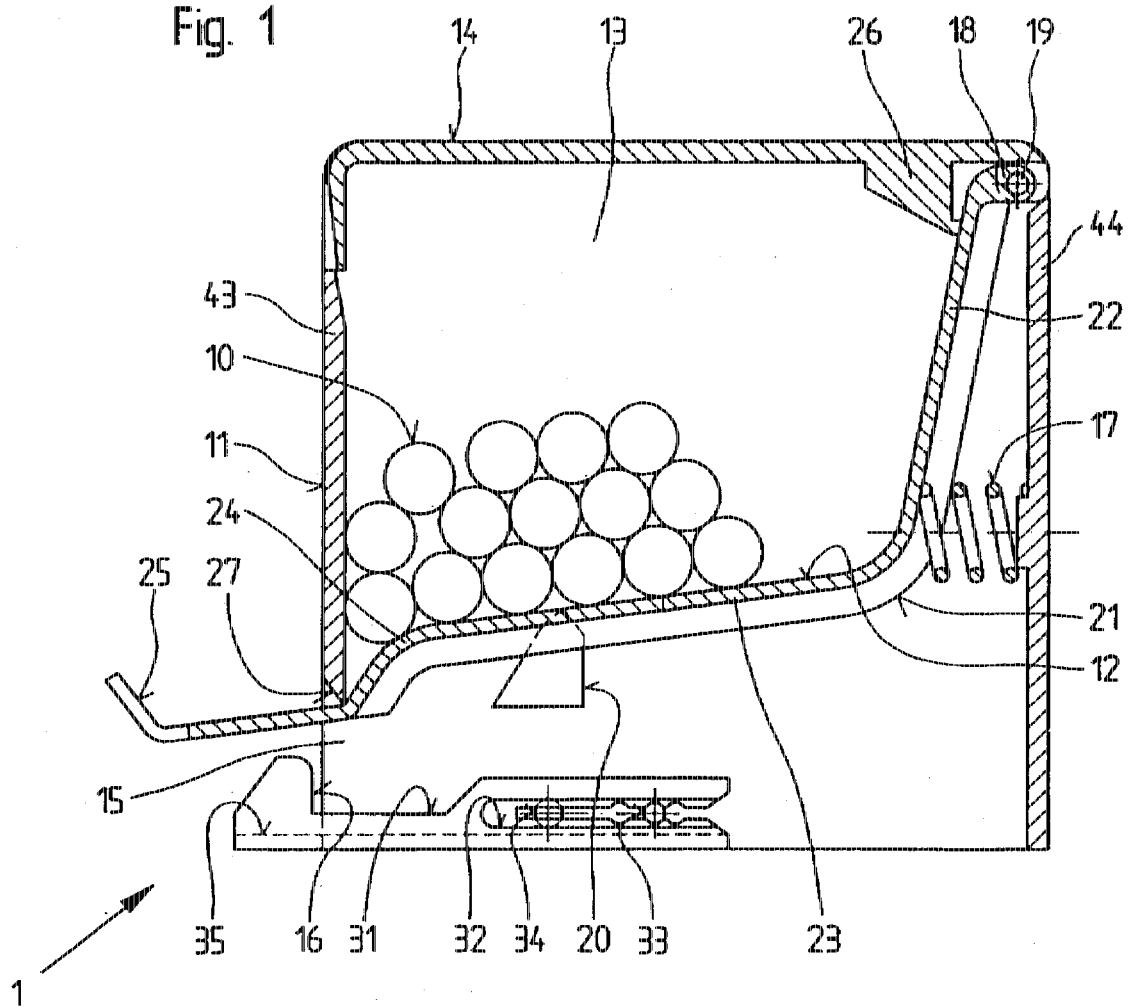
FIG. 1 is a cross-sectional view, in a position of rest, of one exemplary embodiment of the inventive dispenser.
Figure 2:
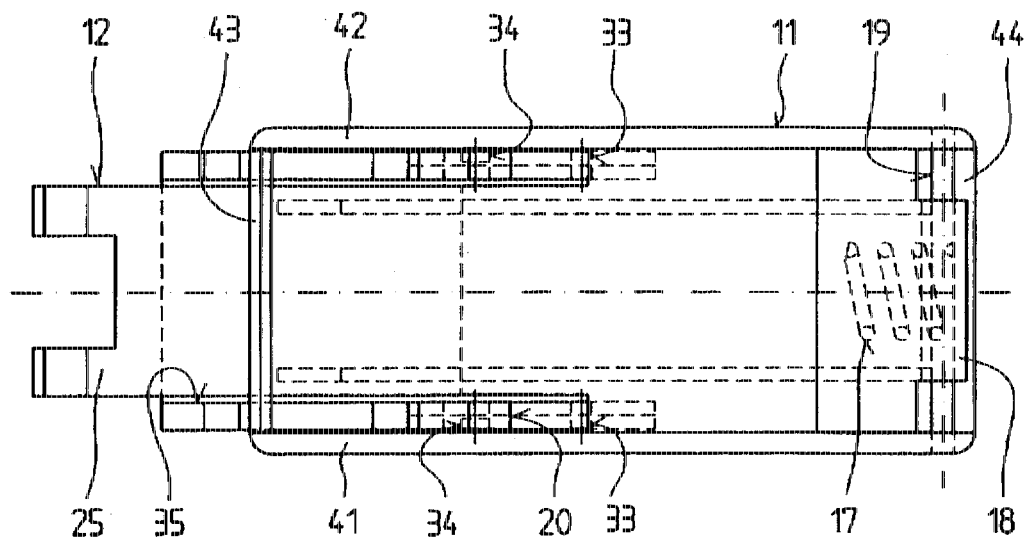
FIG. 2 is a top view of the apparatus of FIG. 1.

The dispenser of the present invention is characterized primarily in that the housing has a base that supports the rolls of wadding or similar rod-like members and that is disposed in the housing in such a way that it is movable against the force of one or more return spring means, the base having a narrow side that extends entirely or partially through the discharge opening.

One end of the base can be connected to the housing or can be guided in the housing in such a way that it can be raised or lowered. In this connection, it is expedient to embody the base as an angular member that defines the receiving chamber of the housing, with that leg of the angular member that is disposed opposite from the discharge opening being pivotably connected to the housing in the upper edge region thereof, for example by means of a pivot pin.

To displace or move the base, a displacement member is provided that acts upon the base either directly or through the intervention of an intermediate member, or is disposed on the base. The displacement member can be a lid that is placed upon the housing and that together with the base is pivotably connected to the housing and by means of a projection or similar intermediate member formed thereon cooperates with the base. However, it is also possible for the displacement member to be formed by a handle member that projects out of or beyond the housing and that is disposed on the base, preferably in the region of the pivot pin that supports the base.

It is furthermore suitable to provide the base, on that side that extends through the discharge opening, with a receiving tray that is located in front of the housing for receiving a rod-like member; another possibility is to provide the housing itself with a stationary receiving tray that is disposed in front of the discharge opening.

It is furthermore advantageous for the base, in the region ahead of the discharge opening of the housing, to be provided with a preferably convexly curved bent portion that projects into the receiving chamber and that is spaced from the discharge opening by a distance equal to approximately the diameter of the rolls of wadding or rod-like members that are stored in the housing. It is also advantageous for one or both inner walls of the housing to be provided with one or more wedge-shaped projections that preferably extend over the range of movement of the base.

To ensure that at any given time only a single roll of wadding or rod-like member can be removed from the apparatus, the discharge opening of the housing should have associated therewith, on the underside and in front of the opening, an abutment means that is preferably embodied as a protuberance and should have a recessed portion for accommodating the receiving tray that is provided on the base; the abutment means can be connected to the housing in such a way that it is movable in the longitudinal direction of the housing.

Pursuant to another specific of the present invention, the abutment means can also be formed on a slide means that is provided with a slot-like recess and can be arrested at varying distances relative to the discharge opening by means of stop means, such as pins, that engage in the recess.

That wall of the housing that faces the abutment means, cooperates with the base, and defines the discharge opening can be provided with an outwardly inclined slanted surface. Furthermore, a receiving tray can be provided on the abutment means on that side thereof that faces away from the housing.

Where the base is embodied as an angular member, the return springs that act upon the base of the housing should be disposed between the leg of the base that is pivotably mounted to the housing and the housing, whereby the return springs can also be embodied as leaf-type springs that are molded on the housing or are molded on the base and rest against the housing.

The inventive apparatus for dispensing rolls of wadding or similar rod-like members ensures that the rod-like members that are stored in the housing can not only be removed from the housing without difficulty, but also that the rod-like members disposed in the housing are protected against contamination. In particular, in order to remove rod-like members it is merely necessary to actuate the displacement member, for example the lid of the housing, in order to eject a rod-like member by means of the base that is operatively connected to the displacement member. And since the base extends through the discharge opening and hence rests against a wall of the housing, the discharge opening is opened for only a short period of time during the movement of the base. Furthermore, the rod-like member that is ejected from the housing and is introduced into a receiving tray cannot be retracted back into the housing, thereby substantially precluding contamination of the rod-like members that are stored in the housing.

In addition to the ease of operation of the inventively embodied dispenser, this apparatus has the further advantage that it can be used in a diversified manner also for rod-like members that have different diameters, whereby the manufacture of the apparatus requires only slight capital expenditures. In particular, the housing and the other components can be economically made from plastic, and the discharge opening of the housing and the abutment means associated therewith can be adapted to the respective diameter of the rod-like members that are stored in the housing. Thus, the removal of respectively only a single roll of wadding or similar rod-like member that is stored in the housing is made considerably easier with the inventive configuration.

Further specific features of the present invention will be described in detail subsequently.

DESCRIPTION OF PREFERRED EMBODIMENTS

Referring now to the drawings in detail, the apparatus illustrated in FIGS. 1 to 5, and designated generally by the reference numeral 1 and 1', serves for the discharge of rolls 10 of wadding, such as of cotton, that are stored in a receiving chamber 13 of a parallelepipedal housing 11. The rolls 10 of wadding can be removed from a discharge opening 15 that is provided in a side wall 43 of the housing 11. For this purpose, a base 12, which can be raised or lowered, is disposed in the housing 11. The base 12 delimits the receiving chamber 13, and in the embodiment illustrated in FIGS. 1 to 4 can be activated with the aid of a lid 14 that is placed upon the housing 11.

In the illustrated embodiment, the base 12 is embodied as an angular member 21, the vertically directed leg 22 of which is pivotably held on the upper region of a wall 44 of the housing 11 by means of a pivot pin 19 that is supported in brackets 18 that are mounted on the housing 11; the lid 14 is also pivotably mounted on the pivot pin 19. In addition, disposed between the leg 22 and the wall 44 of the housing 11 is a return spring 17, so that the leg 23 of the angular member 21, which leg extends approximately horizontally and extends through the discharge opening 15 formed in the opposite wall 43 of the housing 11, is constantly urged against the wall 43. Furthermore, the leg 23 is provided with a convexly curved bent portion 24 that is spaced from the discharge opening 15 by such a distance that at any given time only a single one of the stored rolls 10 of wadding can be discharged.

Furthermore associated with the discharge opening 15 is an abutment or stop means 16 in the form of a protuberance that in the illustrated embodiments is formed on an adjustable slide means 31. In order to be able to realize this arrangement, two inwardly projecting pins 33 and 34 are respectively formed on the side walls 41 and the 42 of the housing 11. The slide means 31 is provided with a notch or recess 32 that is in the form of an elongated slot that is offset and extends in the axial direction. Thus, the slide means 31 can be fixed in various positions that are coordinated with rolls of wadding that have different diameters. In addition, the pins 34 prevent the slide means 31 from being inadvertently shoved into the housing 11.

In addition, a receiving tray 25 is formed on the leg 23 of the angular member 21, and hence on the base 12. The abutment 16 is provided with an appropriate recessed portion 35 so that the receiving tray 25 can be lowered through the abutment 16. Furthermore, in order to prevent the rolls 10 of wadding from lying at an angle or forming bridges in the receiving chamber 13, inwardly projecting, wedge-shaped projections 20 are formed on the side walls 41 and 42 and extend over the range of movement of the pivotably mounted base 12.

If, as shown in FIG. 3, the lid 14 of the housing 11 is pressed down manually, the base 12, due to the fact that a rib 26 that acts upon the base 12 is mounted on the inner side of the lid 14 and hence operatively interconnects the lid 14 with the base 12, is pivoted about the pivot pin 19 against the force of the return spring 17 and is hence moved downwardly. As a result, one of the stored rolls of wadding 10' rests against the abutment 16. If no more force is exerted upon the lid 14, the force of the return spring 17 automatically returns the base 12, and hence the lid 14, into the starting position, as shown in FIG. 4. In so doing, the roll of wadding 10' that rests against the abutment 16 rolls into the receiving tray 25 that is provided on the leg 23, whereupon the roll 10' can easily be removed from the apparatus 1. Discharge of the roll 10' of wadding is enhanced by embodying that surface of the discharge opening 15 that faces the abutment 16 as a slanted surface 27.

Figure 5:
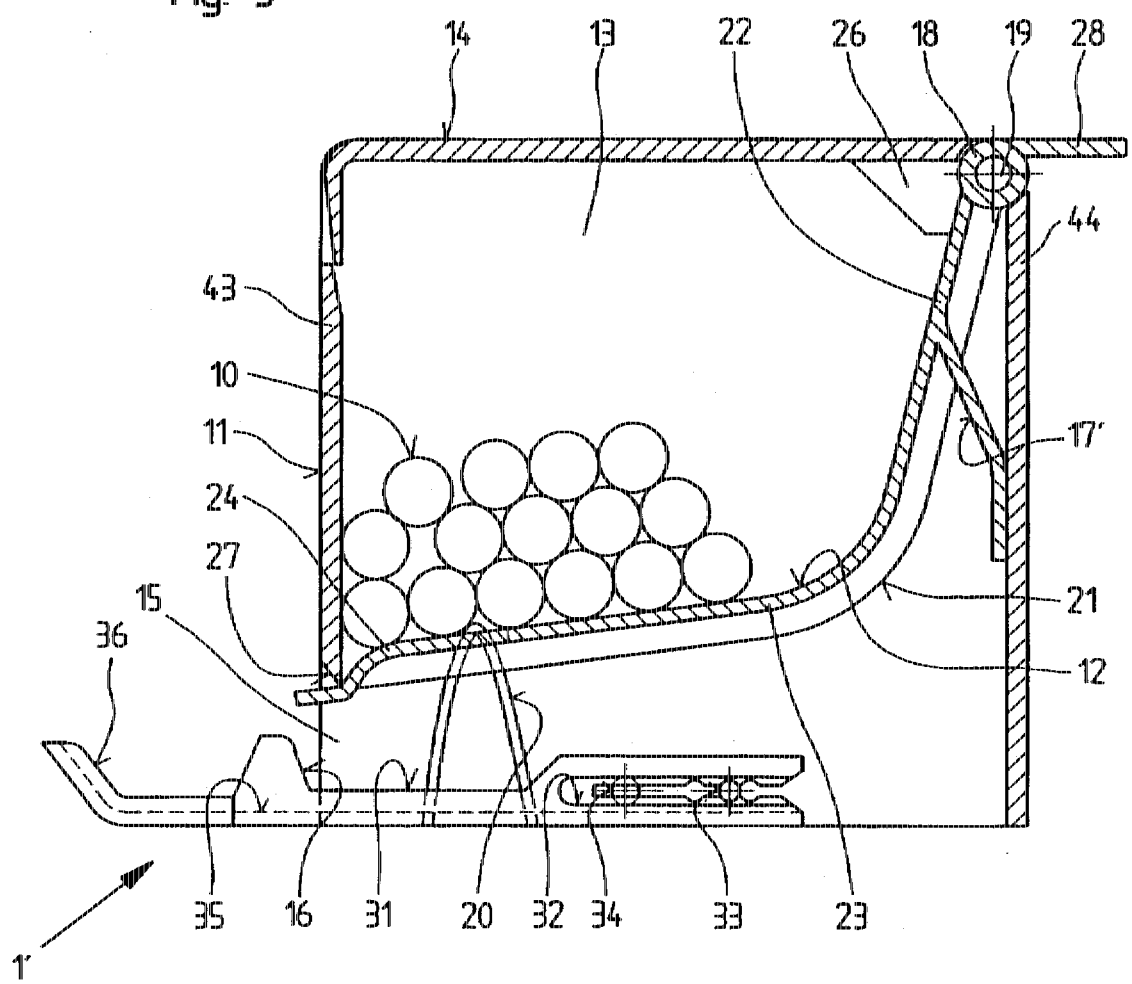
FIG. 5 is a cross-sectional view of a second exemplary embodiment of the inventive dispenser.
Figure 5A:
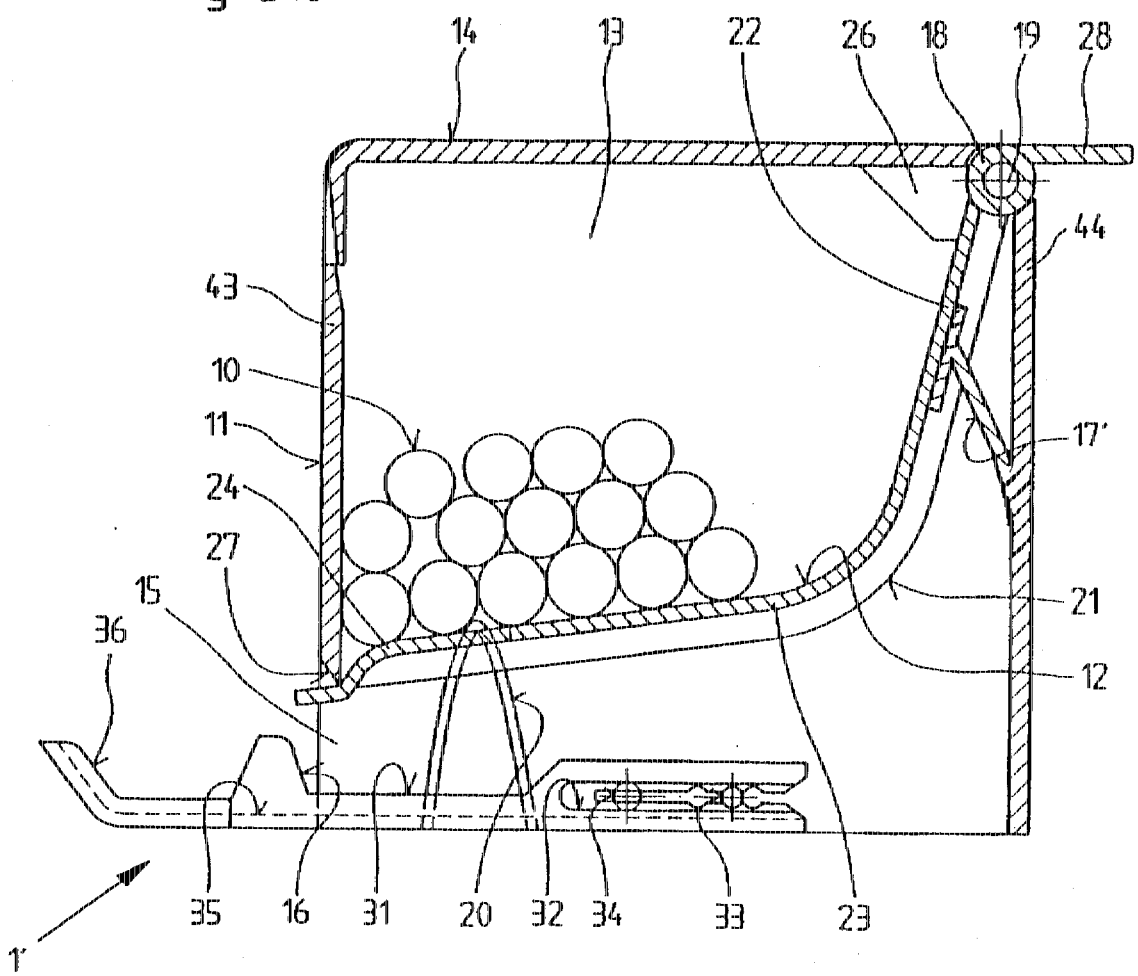
FIG. 5a is a modified embodiment of the spring of FIG. 5.

In the modified embodiment of the apparatus 1' illustrated in FIG. 5, the movement or displacement member that acts upon the base 12 is in the form of a handle member 28 that is mounted directly to the base 12 in the region of the pivot pin 19 and extends out of the housing 11. In this embodiment, the return spring 17' that acts upon the base 12 is embodied as a leaf-type spring that is molded onto the wall 44 of the housing 11, although as shown in FIG. 5, the leaf-type spring 17' could also be molded on the base 12 (FIG. 5a). In addition, the leg 23 of the angular member 21 is shorter in this embodiment, and a stationary receiving tray 36 is formed on the slide means 31. The rolls 10 of wadding that are to be individually removed from the apparatus 1' are lifted over the abutment 16 by the base 12 when the latter is returned to its starting position, whereupon the roll 10 rolls into the receiving tray 36.

The present invention is, of course, in no way restricted to the specific disclosure of the specification and drawings, but also encompasses any modifications within the scope of the appended claims.

What I claim is:

1. An apparatus for dispensing rod-like members that are stored in a parallelepipedal housing that includes a narrow side that is provided with a discharge opening that is disposed parallel to said stored rod-like members, wherein said housing further comprises a movable base for carrying said rod-like members, return spring means pressing against said base, said base having a narrow side that extends at least partially through said discharge opening, and a displacement member that acts upon said base to effect movement thereof, wherein at least one side wall of said housing, on an inner side thereof, is provided with at least one wedge-shaped projection that preferably extends over the range of movement of said base.

2. An apparatus according to claim 1, wherein an end of said base remote from said narrow side thereof is supported by said housing.

3. An apparatus according to claim 2, wherein said base is an angular member that defines a receiving chamber for said rod-like members in said housing, said angular member having a first leg that extends at least partially through said discharge opening, and a second leg that remote from said discharge opening is pivotably connected to an upper edge region of said housing.

4. An apparatus according to claim 3, wherein said displacement member is a lid that is disposed on said housing and is pivotably connected thereto together with said base, a projection being provided on said lid for acting on said base to effect said movement thereof.

5. An apparatus according to claim 3, wherein said first leg of said angular member that extends through said discharge opening has disposed thereon a receiving tray for one of said rod-like members.

6. An apparatus according to claim 3, wherein said return spring means is disposed between said second leg of said base and said housing.

7. An apparatus according to claim 6, wherein said return spring means is a leaf-type spring that is molded on said housing and presses against said base.

8. An apparatus according to claim 6, wherein said return spring means is a leaf-type spring that is molded on said base and rests against said housing.

9. An apparatus according to claim 1, wherein said displacement member is a handle member disposed on said base and projecting beyond said housing.

10. An apparatus according to claim 1, wherein a stationary receiving tray is disposed on said housing in front of said discharge opening.

11. An apparatus according to claim 1, wherein said base, within said housing and in the vicinity of said discharge opening, is provided with a curved or bent portion that projects into said receiving chamber.

12. An apparatus according to claim 11, wherein said bent portion of said base is spaced from said discharge opening by a distance that during a dispensing operation corresponds approximately to a diameter of said rod-like members stored in said housing.

13. An apparatus according to claim 1, wherein abutment means is provided in front of said discharge opening at a bottom side thereof.

14. An apparatus according to claim 13, wherein said abutment means is provided with a recessed portion for accommodating a receiving tray provided on said base.

15. An apparatus according to claim 13, wherein said abutment means is disposed in said housing in such a way as to be movable in a longitudinal direction thereof.

16. An apparatus according to claim 15, wherein said abutment means is formed on a slide means that is provided with a slot-like recess, and wherein said housing is provided with stop means for engaging said recess to arrest said slide means at varying distances relative to said discharge opening.

17. An apparatus according to claim 13, wherein a wall of said housing that delimits said discharge opening, faces said abutment means, and cooperates with said base is provided with a slanted surface that is inclined outwardly and away from, said base.

18. An apparatus according to claim 13, wherein said abutment means, on a side thereof that faces away from said housing, is provided with a receiving tray.

* * * * *